United States Patent
Henley et al.

(10) Patent No.: US 11,185,213 B2
(45) Date of Patent: Nov. 30, 2021

(54) SCOPE SENSING IN A LIGHT CONTROLLED ENVIRONMENT

(71) Applicant: DePuy Synthes Products, Inc., Raynham, MA (US)

(72) Inventors: Jeremiah D. Henley, Salt Lake City, UT (US); Donald M. Wichern, Salt Lake City, UT (US); Joshua D. Talbert, Salt Lake City, UT (US); Laurent Blanquart, Westlake Village, CA (US); John Richardson, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 314 days.

(21) Appl. No.: 16/241,118

(22) Filed: Jan. 7, 2019

(65) Prior Publication Data

US 2019/0133416 A1 May 9, 2019

Related U.S. Application Data

(62) Division of application No. 14/214,334, filed on Mar. 14, 2014, now Pat. No. 10,251,530.

(Continued)

(51) Int. Cl.
*A61B 1/00* (2006.01)
*A61B 1/045* (2006.01)
(Continued)

(52) U.S. Cl.
CPC ...... *A61B 1/00006* (2013.01); *A61B 1/00009* (2013.01); *A61B 1/00036* (2013.01);
(Continued)

(58) Field of Classification Search
CPC ............ A61B 1/00025; A61B 1/00036; A61B 1/00006; A61B 1/128; A61B 2017/00057; A61B 2017/00066
(Continued)

(56) References Cited

U.S. PATENT DOCUMENTS 3,666,885 A 5/1972 Hemsley et al.
4,011,403 A 3/1977 Epstein et al.
(Continued)

FOREIGN PATENT DOCUMENTS

CN 1520696 A 8/2004
CN 101079966 A 11/2007
(Continued)

OTHER PUBLICATIONS

Jack, Keith "Video Demystified: A Handbook for the Digital Engineer," 2007 Fifth Edition. ISBN: 978-0-7506-8395-1, p. 21.
(Continued)

*Primary Examiner* — Alexandra L Newton
*Assistant Examiner* — Jae Woo
(74) *Attorney, Agent, or Firm* — Terrence J. Edwards; TechLaw Ventures, PLLC

(57) ABSTRACT

The disclosure extends to methods, systems, and computer program products for detecting whether an illumination source of an endoscope is in use (inside the body of a patient) versus not in use (outside the body of a patient). The disclosure relies on the fact that the working environment is lit solely by the endoscope and its components. Thus, communication between the illumination or light source controller and the imaging device, such as a surgical camera, is required. When the illumination or light source is turned off and the endoscope is outside the body, a sensor will detect ambient light alerting the illumination source controller that it is outside the body, which then keeps the
(Continued)

illumination source off or at a low intensity level. Conversely, when the illumination source is turned off and the endoscope is inside the body, the sensor will not detect any light (or will detect only a very low level of light). Based on this logic, if the imaging device, such as a camera, knows that the light is off during a specific period of time the frame(s) from that time period can be analyzed and the level of light gathered in the frame(s) will show the scope location either inside or outside of the body.

25 Claims, 9 Drawing Sheets

Related U.S. Application Data

(60) Provisional application No. 61/791,685, filed on Mar. 15, 2013.

(51) Int. Cl.
*A61B 1/06* (2006.01)
*G02B 23/24* (2006.01)

(52) U.S. Cl.
CPC ............... *A61B 1/045* (2013.01); *A61B 1/06* (2013.01); *G02B 23/2484* (2013.01)

(58) Field of Classification Search
USPC .......................................... 600/117, 178, 180
See application file for complete search history.

(56) References Cited

U.S. PATENT DOCUMENTS

| | | | |
|---|---|---|---|
| 4,356,534 A * | 10/1982 | Hattori | A61B 1/00117 362/276 |
| 4,363,963 A | 12/1982 | Ando | |
| 4,433,675 A | 2/1984 | Konoshima | |
| 4,436,095 A | 3/1984 | Kruger | |
| 4,473,839 A | 9/1984 | Noda | |
| 4,644,403 A | 2/1987 | Sakai et al. | |
| 4,651,226 A | 3/1987 | Motoori et al. | |
| 4,692,606 A | 9/1987 | Sakai et al. | |
| 4,740,837 A | 4/1988 | Yanagisawa et al. | |
| 4,741,327 A | 5/1988 | Yabe | |
| 4,742,388 A | 5/1988 | Cooper et al. | |
| 4,745,471 A | 5/1988 | Takamura et al. | |
| 4,773,396 A | 9/1988 | Okazaki | |
| 4,782,386 A | 11/1988 | Ams et al. | |
| 4,786,965 A | 11/1988 | Yabe | |
| 4,832,003 A | 5/1989 | Yabe | |
| 4,845,555 A | 7/1989 | Yabe et al. | |
| 4,853,772 A | 8/1989 | Kikuchi | |
| 4,853,773 A | 8/1989 | Hibino et al. | |
| 4,865,018 A * | 9/1989 | Kanno | A61B 1/05 600/109 |
| 4,866,526 A | 9/1989 | Ams et al. | |
| 4,884,133 A * | 11/1989 | Kanno | A61B 1/00059 348/68 |
| 4,884,134 A | 11/1989 | Tsuji et al. | |
| 4,908,701 A | 3/1990 | Udagawa | |
| 4,918,521 A | 4/1990 | Yabe et al. | |
| 4,924,856 A * | 5/1990 | Noguchi | A61B 1/042 348/70 |
| 4,938,205 A | 7/1990 | Nudelman | |
| 4,942,473 A | 7/1990 | Zeevi et al. | |
| 4,947,246 A | 8/1990 | Kikuchi | |
| 4,953,539 A | 9/1990 | Nakamura et al. | |
| 4,959,710 A | 9/1990 | Uehara et al. | |
| 4,963,960 A * | 10/1990 | Takami | A61B 1/05 348/69 |
| 5,001,556 A | 3/1991 | Nakamura et al. | |
| 5,016,975 A | 5/1991 | Sasaki et al. | |
| 5,021,888 A | 6/1991 | Kondou et al. | |
| 5,047,846 A | 9/1991 | Uchiyama et al. | |
| RE33,854 E | 3/1992 | Adair | |
| 5,103,497 A | 4/1992 | Hicks | |
| 5,111,804 A | 5/1992 | Funakoshi | |
| 5,133,035 A | 7/1992 | Hicks | |
| 5,187,572 A | 2/1993 | Nakamura et al. | |
| 5,188,094 A | 2/1993 | Adair | |
| 5,196,938 A | 3/1993 | Blessinger | |
| 5,200,838 A | 4/1993 | Nudelman et al. | |
| 5,220,198 A | 6/1993 | Tsuji | |
| 5,228,430 A | 7/1993 | Sakamoto | |
| 5,233,416 A | 8/1993 | Inoue | |
| 5,241,170 A | 8/1993 | Field, Jr. et al. | |
| 5,255,087 A | 10/1993 | Nakamura et al. | |
| 5,264,925 A | 11/1993 | Shipp et al. | |
| 5,313,306 A | 5/1994 | Kuban et al. | |
| 5,325,847 A | 7/1994 | Matsuno | |
| 5,365,268 A | 11/1994 | Minami | |
| 5,402,768 A | 4/1995 | Adair | |
| 5,408,268 A | 4/1995 | Shipp | |
| 5,411,020 A | 5/1995 | Ito | |
| 5,427,087 A | 6/1995 | Ito et al. | |
| 5,454,366 A | 10/1995 | Ito et al. | |
| 5,494,483 A | 2/1996 | Adair | |
| 5,523,786 A | 6/1996 | Parulski | |
| 5,550,595 A | 8/1996 | Hannah | |
| 5,558,841 A * | 9/1996 | Nakagawa | A61B 1/00057 134/104.1 |
| 5,594,497 A | 1/1997 | Ahern et al. | |
| 5,627,584 A * | 5/1997 | Nishikori | A61B 1/123 348/65 |
| 5,658,238 A * | 8/1997 | Suzuki | A61B 1/00039 600/146 |
| 5,665,959 A | 9/1997 | Fossum et al. | |
| 5,704,836 A | 1/1998 | Norton et al. | |
| 5,730,702 A | 3/1998 | Tanaka et al. | |
| 5,734,418 A | 3/1998 | Danna | |
| 5,748,234 A | 5/1998 | Lippincott | |
| 5,749,830 A | 5/1998 | Kaneko et al. | |
| 5,754,313 A | 5/1998 | Pelchy et al. | |
| 5,783,909 A | 7/1998 | Hochstein | |
| 5,784,099 A | 7/1998 | Lippincott | |
| 5,857,963 A | 1/1999 | Pelchy et al. | |
| 5,887,049 A | 3/1999 | Fossum | |
| 5,924,978 A * | 7/1999 | Koeda | G02B 6/0006 600/131 |
| 5,929,901 A | 7/1999 | Adair et al. | |
| 5,949,483 A | 9/1999 | Fossum et al. | |
| 5,957,834 A * | 9/1999 | Mochida | A61B 1/045 348/E5.037 |
| 5,986,693 A | 11/1999 | Adair et al. | |
| 6,023,315 A | 2/2000 | Harrold et al. | |
| 6,038,067 A | 3/2000 | George | |
| 6,043,839 A | 3/2000 | Adair et al. | |
| 6,139,489 A | 10/2000 | Wampler et al. | |
| 6,141,505 A | 10/2000 | Miyata et al. | |
| 6,142,930 A | 11/2000 | Ito et al. | |
| 6,166,768 A | 12/2000 | Fossum et al. | |
| 6,184,922 B1 | 2/2001 | Saito et al. | |
| 6,184,940 B1 | 2/2001 | Sano | |
| 6,215,517 B1 | 3/2001 | Takahashi et al. | |
| 6,222,175 B1 | 4/2001 | Krymski | |
| 6,239,456 B1 | 5/2001 | Berezin et al. | |
| 6,272,269 B1 | 8/2001 | Naum | |
| 6,275,255 B1 | 8/2001 | Adair et al. | |
| 6,292,220 B1 | 9/2001 | Ogawa et al. | |
| 6,294,775 B1 * | 9/2001 | Seibel | A61B 1/0008 250/208.1 |
| 6,310,642 B1 | 10/2001 | Adair et al. | |
| 6,320,331 B1 | 11/2001 | Iida et al. | |
| 6,331,156 B1 | 12/2001 | Haefele et al. | |
| 6,389,205 B1 * | 5/2002 | Muckner | A61B 1/00117 362/574 |
| 6,416,463 B1 | 7/2002 | Tsuzuki et al. | |
| 6,429,953 B1 | 8/2002 | Feng | |
| 6,444,970 B1 | 9/2002 | Barbato | |
| 6,445,022 B1 | 9/2002 | Barna et al. | |
| 6,445,139 B1 | 9/2002 | Marshall et al. | |
| 6,464,633 B1 | 10/2002 | Hosoda et al. | |

(56) References Cited

U.S. PATENT DOCUMENTS

| | | | |
|---|---|---|---|
| 6,466,618 B1 | 10/2002 | Messing et al. |
| 6,485,414 B1 | 11/2002 | Neuberger |
| 6,512,280 B2 | 1/2003 | Chen et al. |
| 6,567,115 B1 | 5/2003 | Miyashita et al. |
| 6,627,474 B2 | 9/2003 | Barna et al. |
| 6,631,230 B1 | 10/2003 | Campbell |
| 6,659,940 B2 | 12/2003 | Adler |
| 6,665,013 B1 | 12/2003 | Fossum et al. |
| 6,677,992 B1 | 1/2004 | Matsumoto et al. |
| 6,687,534 B2 | 2/2004 | Tsujita |
| 6,690,466 B2 | 2/2004 | Miller et al. |
| 6,692,431 B2 | 2/2004 | Kazakevich |
| 6,707,499 B1 | 3/2004 | Kung et al. |
| 6,772,181 B1 | 8/2004 | Fu et al. |
| 6,773,392 B2 | 8/2004 | Kikuchi et al. |
| 6,791,739 B2 | 9/2004 | Ramanujan et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,836,288 B1 * | 12/2004 | Lewis | H04N 5/2352 348/221.1 |
| 6,838,653 B2 | 1/2005 | Campbell et al. |
| 6,841,947 B2 | 1/2005 | Berg-johansen |
| 6,847,399 B1 | 1/2005 | Ang |
| 6,856,712 B2 | 2/2005 | Fauver et al. |
| 6,873,363 B1 | 3/2005 | Barna et al. |
| 6,879,340 B1 | 4/2005 | Chevallier |
| 6,899,675 B2 | 5/2005 | Cline et al. |
| 6,900,829 B1 | 5/2005 | Orzawa et al. |
| 6,906,745 B1 | 6/2005 | Fossum et al. |
| 6,921,920 B2 | 7/2005 | Kazakevich |
| 6,933,974 B2 | 8/2005 | Lee |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,977,733 B2 | 12/2005 | Denk et al. |
| 6,982,740 B2 | 1/2006 | Adair et al. |
| 6,998,594 B2 | 2/2006 | Gaines et al. |
| 6,999,118 B2 | 2/2006 | Suzuki |
| 7,009,634 B2 | 3/2006 | Iddan et al. |
| 7,009,648 B2 | 3/2006 | Lauxtermann et al. |
| 7,030,904 B2 | 4/2006 | Adair et al. |
| 7,037,259 B2 | 5/2006 | Hakamata et al. |
| 7,068,878 B2 | 6/2006 | Crossman-Bosworth et al. |
| 7,071,979 B1 | 7/2006 | Ohtani et al. |
| 7,079,178 B2 | 7/2006 | Hynecek |
| 7,102,682 B2 | 9/2006 | Baer |
| 7,105,371 B2 | 9/2006 | Fossum et al. |
| 7,106,377 B2 | 9/2006 | Bean et al. |
| 7,119,839 B1 | 10/2006 | Mansoorian |
| 7,151,568 B2 | 12/2006 | Kawachi et al. |
| 7,159,782 B2 | 1/2007 | Johnston et al. |
| 7,184,084 B2 | 2/2007 | Glenn |
| 7,189,226 B2 | 3/2007 | Auld et al. |
| 7,189,961 B2 | 3/2007 | Johnston et al. |
| 7,208,983 B2 | 4/2007 | Imaizumi et al. |
| 7,252,236 B2 | 8/2007 | Johnston et al. |
| 7,258,663 B2 | 8/2007 | Doguchi et al. |
| 7,261,687 B2 | 8/2007 | Yang |
| 7,280,139 B2 | 10/2007 | Pahr et al. |
| 7,298,938 B2 | 11/2007 | Johnston |
| 7,312,879 B2 | 12/2007 | Johnston |
| 7,319,478 B2 | 1/2008 | Dolt et al. |
| 7,355,155 B2 | 4/2008 | Wang |
| 7,356,198 B2 | 4/2008 | Chauville et al. |
| 7,365,768 B1 | 4/2008 | Ono et al. |
| 7,369,140 B1 | 5/2008 | King et al. |
| 7,369,176 B2 | 5/2008 | Sonnenschein et al. |
| 7,385,708 B2 * | 6/2008 | Ackerman | A61B 1/042 356/603 |
| 7,455,638 B2 | 11/2008 | Ogawa et al. |
| 7,470,229 B2 | 12/2008 | Ogawa et al. |
| 7,476,197 B2 | 1/2009 | Wiklof et al. |
| 7,532,760 B2 | 5/2009 | Kaplinsky et al. |
| 7,540,645 B2 | 5/2009 | Choi |
| 7,544,163 B2 | 6/2009 | MacKinnon et al. |
| 7,545,434 B2 | 6/2009 | Bean et al. |
| 7,564,935 B2 | 7/2009 | Suzuki |
| 7,567,291 B2 | 7/2009 | Bechtel et al. |
| 7,573,516 B2 | 8/2009 | Krymski et al. |
| 7,573,519 B2 | 8/2009 | Phan et al. |
| 7,583,872 B2 | 9/2009 | Seibel et al. |
| 7,608,807 B2 * | 10/2009 | Hick | G01J 1/4204 250/205 |
| 7,616,238 B2 | 11/2009 | Avni et al. |
| 7,630,008 B2 | 12/2009 | Sarwari |
| 7,744,528 B2 | 6/2010 | Wallace et al. |
| 7,783,133 B2 | 8/2010 | Dunki-Jacobs et al. |
| 7,784,697 B2 | 8/2010 | Johnston et al. |
| 7,791,009 B2 | 9/2010 | Johnston et al. |
| 7,792,378 B2 | 9/2010 | Liege et al. |
| 7,794,394 B2 | 9/2010 | Frangioni |
| 7,796,870 B2 * | 9/2010 | Wang | A61B 1/00096 396/14 |
| 7,813,538 B2 | 10/2010 | Carroll et al. |
| 7,901,974 B2 | 3/2011 | Venezia et al. |
| 7,914,447 B2 | 3/2011 | Kanai |
| 7,916,193 B2 | 3/2011 | Fossum |
| 7,935,050 B2 | 5/2011 | Luanava et al. |
| 7,944,566 B2 | 5/2011 | Xie |
| 7,952,096 B2 | 5/2011 | Rhodes |
| 7,969,097 B2 | 6/2011 | Van De Ven |
| 7,995,123 B2 | 8/2011 | Lee et al. |
| 8,018,589 B2 * | 9/2011 | MacKinnon | G01J 3/12 356/300 |
| 8,040,394 B2 | 10/2011 | Fossum et al. |
| 8,054,339 B2 | 11/2011 | Fossum et al. |
| 8,059,174 B2 | 11/2011 | Mann et al. |
| 8,100,826 B2 | 1/2012 | MacKinnon et al. |
| 8,159,584 B2 | 4/2012 | Iwabuchi et al. |
| 8,193,542 B2 | 6/2012 | Machara |
| 8,194,061 B2 * | 6/2012 | Wang | H01M 10/44 345/211 |
| 8,212,884 B2 | 7/2012 | Seibel et al. |
| 8,213,698 B2 * | 7/2012 | Wang | H04N 5/232411 382/128 |
| 8,231,522 B2 | 7/2012 | Endo et al. |
| 8,300,111 B2 | 10/2012 | Iwane |
| 8,372,003 B2 * | 2/2013 | St. George | A61B 1/00009 600/178 |
| 8,382,662 B2 | 2/2013 | Soper et al. |
| 8,396,535 B2 | 3/2013 | Wang et al. |
| 8,423,110 B2 | 4/2013 | Barbato et al. |
| 8,471,938 B2 | 6/2013 | Altice, Jr. et al. |
| 8,476,575 B2 | 7/2013 | Mokhuatyuk |
| 8,482,823 B2 | 7/2013 | Cheng |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,559,743 B2 | 10/2013 | Liege et al. |
| 8,582,011 B2 | 11/2013 | Dosluoglu |
| 8,602,971 B2 | 12/2013 | Farr |
| 8,605,177 B2 | 12/2013 | Rossi et al. |
| 8,610,808 B2 | 12/2013 | Prescher et al. |
| 8,614,754 B2 | 12/2013 | Fossum |
| 8,625,016 B2 | 1/2014 | Fossum et al. |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,668,639 B2 * | 3/2014 | Kagaya | A61B 1/045 600/180 |
| 8,675,125 B2 | 3/2014 | Cossairt et al. |
| 8,698,887 B2 | 4/2014 | Makino et al. |
| 8,836,834 B2 | 9/2014 | Hashimoto et al. |
| 8,848,063 B2 | 9/2014 | Jo et al. |
| 8,858,425 B2 | 10/2014 | Farr et al. |
| 8,885,034 B2 | 11/2014 | Adair et al. |
| 8,941,308 B2 * | 1/2015 | Briggs | H05B 45/00 315/158 |
| 9,182,337 B2 | 11/2015 | Kamee et al. |
| 9,349,764 B1 | 5/2016 | Lee et al. |

(56) References Cited

U.S. PATENT DOCUMENTS

| | | |
|---|---|---|
| 9,509,917 B2 | 11/2016 | Blanquart et al. |
| 9,516,239 B2 | 12/2016 | Blanquart et al. |
| 9,634,878 B1 | 4/2017 | Bench et al. |
| 9,762,879 B2 | 9/2017 | Blanquart et al. |
| 9,777,913 B2 | 10/2017 | Talbert et al. |
| 10,084,944 B2 | 9/2018 | Henley et al. |
| 10,251,530 B2 | 4/2019 | Henley et al. |
| 10,277,875 B2 | 4/2019 | Blanquart et al. |
| 2001/0016064 A1 | 8/2001 | Tsuruoka et al. |
| 2001/0017649 A1 | 8/2001 | Yaron |
| 2001/0030744 A1 | 10/2001 | Chang |
| 2001/0055462 A1 | 12/2001 | Seibel |
| 2002/0045801 A1* | 4/2002 | Niida .............. A61B 1/00057 600/118 |
| 2002/0054219 A1 | 5/2002 | Jaspers |
| 2002/0064341 A1 | 5/2002 | Fauver et al. |
| 2002/0080248 A1 | 6/2002 | Adair et al. |
| 2002/0080359 A1 | 6/2002 | Denk et al. |
| 2002/0140844 A1 | 10/2002 | Kurokawa et al. |
| 2002/0158976 A1* | 10/2002 | Vni .................. A61B 1/045 348/243 |
| 2002/0158986 A1 | 10/2002 | Baer |
| 2003/0007087 A1 | 1/2003 | Hakamata et al. |
| 2003/0007686 A1 | 1/2003 | Roever |
| 2003/0107664 A1* | 6/2003 | Suzuki .............. H04N 5/2357 348/296 |
| 2003/0189663 A1 | 10/2003 | Dolt et al. |
| 2003/0189705 A1 | 10/2003 | Pardo |
| 2004/0082833 A1 | 4/2004 | Adler et al. |
| 2004/0170712 A1 | 9/2004 | Sadek El Mogy |
| 2004/0215059 A1* | 10/2004 | Homan .............. A61B 1/041 600/160 |
| 2005/0009982 A1 | 1/2005 | Inagaki et al. |
| 2005/0027164 A1 | 2/2005 | Barbato et al. |
| 2005/0038322 A1 | 2/2005 | Banik |
| 2005/0041571 A1 | 2/2005 | Ichihara et al. |
| 2005/0052680 A1* | 3/2005 | Okamura .......... H04N 1/00835 358/1.14 |
| 2005/0113641 A1 | 5/2005 | Bala |
| 2005/0122530 A1 | 6/2005 | Denk et al. |
| 2005/0151866 A1 | 7/2005 | Ando et al. |
| 2005/0200291 A1 | 9/2005 | Naugler, Jr. et al. |
| 2005/0234302 A1 | 10/2005 | MacKinnon et al. |
| 2005/0237384 A1 | 10/2005 | Jess et al. |
| 2005/0261552 A1 | 11/2005 | Mori et al. |
| 2005/0267329 A1 | 12/2005 | Konstorum et al. |
| 2005/0277808 A1 | 12/2005 | Sonnenschein et al. |
| 2005/0288546 A1 | 12/2005 | Sonnenschein et al. |
| 2006/0038823 A1 | 2/2006 | Arcas |
| 2006/0069314 A1 | 3/2006 | Farr |
| 2006/0087841 A1 | 4/2006 | Chern et al. |
| 2006/0106284 A1* | 5/2006 | Shouji .............. A61B 1/00011 600/118 |
| 2006/0197664 A1 | 9/2006 | Zhang et al. |
| 2006/0202036 A1 | 9/2006 | Wang et al. |
| 2006/0221250 A1 | 10/2006 | Rossbach et al. |
| 2006/0226231 A1 | 10/2006 | Johnston et al. |
| 2006/0264734 A1 | 11/2006 | Kimoto et al. |
| 2006/0274335 A1 | 12/2006 | Wittenstein |
| 2007/0010712 A1 | 1/2007 | Negishi |
| 2007/0010713 A1* | 1/2007 | Negishi ................ A61B 1/06 600/178 |
| 2007/0029629 A1 | 2/2007 | Yazdi |
| 2007/0041448 A1 | 2/2007 | Miller et al. |
| 2007/0066868 A1* | 3/2007 | Shikii .............. A61B 1/00036 600/118 |
| 2007/0083085 A1* | 4/2007 | Birnkrant ............ A61B 1/07 600/178 |
| 2007/0092283 A1* | 4/2007 | Sugihara .......... G03G 15/5016 399/81 |
| 2007/0129601 A1 | 6/2007 | Johnston et al. |
| 2007/0147033 A1 | 6/2007 | Ogawa et al. |
| 2007/0182723 A1 | 8/2007 | Imai et al. |
| 2007/0182842 A1 | 8/2007 | Sonnenschein et al. |
| 2007/0225560 A1 | 9/2007 | Avni et al. |
| 2007/0244364 A1 | 10/2007 | Luanava et al. |
| 2007/0244365 A1 | 10/2007 | Wiklof |
| 2007/0274649 A1* | 11/2007 | Takahashi .......... G02B 23/2476 385/117 |
| 2007/0276187 A1 | 11/2007 | Wiklof et al. |
| 2007/0279486 A1 | 12/2007 | Bayer et al. |
| 2007/0285526 A1 | 12/2007 | Mann et al. |
| 2007/0293720 A1 | 12/2007 | Bayer |
| 2008/0045800 A2 | 2/2008 | Farr |
| 2008/0049132 A1 | 2/2008 | Suzuki |
| 2008/0088719 A1 | 4/2008 | Jacob et al. |
| 2008/0107333 A1 | 5/2008 | Mazinani et al. |
| 2008/0136953 A1 | 6/2008 | Barnea et al. |
| 2008/0158348 A1 | 7/2008 | Karpen et al. |
| 2008/0164550 A1 | 7/2008 | Chen et al. |
| 2008/0165360 A1 | 7/2008 | Johnston |
| 2008/0167523 A1* | 7/2008 | Uchiyama ............ A61B 5/073 600/114 |
| 2008/0192131 A1 | 8/2008 | Kim et al. |
| 2008/0208077 A1* | 8/2008 | Iddan .................. A61B 1/041 600/582 |
| 2008/0218598 A1 | 9/2008 | Harada et al. |
| 2008/0218615 A1 | 9/2008 | Huang et al. |
| 2008/0218824 A1 | 9/2008 | Johnston et al. |
| 2008/0249369 A1 | 10/2008 | Seibel et al. |
| 2008/0287742 A1* | 11/2008 | St. George .......... A61B 1/00009 600/160 |
| 2009/0012361 A1 | 1/2009 | MacKinnon et al. |
| 2009/0012368 A1 | 1/2009 | Banik |
| 2009/0021588 A1 | 1/2009 | Border et al. |
| 2009/0024000 A1 | 1/2009 | Chen |
| 2009/0028465 A1 | 1/2009 | Pan |
| 2009/0074265 A1 | 3/2009 | Huang et al. |
| 2009/0091645 A1 | 4/2009 | Trimeche et al. |
| 2009/0137893 A1 | 5/2009 | Seibel et al. |
| 2009/0147077 A1 | 6/2009 | Tani et al. |
| 2009/0154886 A1 | 6/2009 | Lewis et al. |
| 2009/0160976 A1 | 6/2009 | Chen et al. |
| 2009/0189530 A1 | 7/2009 | Ashdown et al. |
| 2009/0208143 A1 | 8/2009 | Yoon et al. |
| 2009/0227847 A1 | 9/2009 | Tepper et al. |
| 2009/0232213 A1 | 9/2009 | Jia |
| 2009/0259102 A1 | 10/2009 | Koninckx et al. |
| 2009/0268063 A1 | 10/2009 | Ellis-Monaghan et al. |
| 2009/0274380 A1 | 11/2009 | Wedi |
| 2009/0292168 A1 | 11/2009 | Farr |
| 2009/0309500 A1* | 12/2009 | Reisch ................ B60Q 1/1423 315/158 |
| 2009/0316116 A1 | 12/2009 | Melville et al. |
| 2009/0322912 A1 | 12/2009 | Blanquart |
| 2010/0004513 A1* | 1/2010 | MacKinnon .............. G01J 3/10 600/180 |
| 2010/0026722 A1 | 2/2010 | Kondo |
| 2010/0049180 A1 | 2/2010 | Wells et al. |
| 2010/0069713 A1 | 3/2010 | Endo et al. |
| 2010/0102199 A1 | 4/2010 | Negley et al. |
| 2010/0121142 A1 | 5/2010 | OuYang et al. |
| 2010/0121143 A1 | 5/2010 | Sugimoto et al. |
| 2010/0123775 A1 | 5/2010 | Shibasaki |
| 2010/0134608 A1 | 6/2010 | Shibasaki |
| 2010/0134662 A1 | 6/2010 | Bub |
| 2010/0135398 A1 | 6/2010 | Wittmann et al. |
| 2010/0137684 A1 | 6/2010 | Shibasaki et al. |
| 2010/0149421 A1 | 6/2010 | Lin et al. |
| 2010/0157037 A1 | 6/2010 | Iketani et al. |
| 2010/0157039 A1 | 6/2010 | Sugai |
| 2010/0165087 A1 | 7/2010 | Corso et al. |
| 2010/0171429 A1* | 7/2010 | Garcia .................. H05B 45/12 315/149 |
| 2010/0182446 A1 | 7/2010 | Matsubayashi |
| 2010/0198009 A1 | 8/2010 | Farr et al. |
| 2010/0198134 A1 | 8/2010 | Eckhouse et al. |
| 2010/0201797 A1 | 8/2010 | Shizukuishi et al. |
| 2010/0208056 A1 | 8/2010 | Olsson et al. |
| 2010/0228089 A1 | 9/2010 | Hoffman et al. |
| 2010/0261961 A1 | 10/2010 | Scott et al. |
| 2010/0274082 A1 | 10/2010 | Iguchi et al. |
| 2010/0274090 A1 | 10/2010 | Ozaki et al. |

(56) References Cited

U.S. PATENT DOCUMENTS

| | | |
|---|---|---|
| 2010/0305406 A1 | 12/2010 | Braun et al. |
| 2010/0309333 A1 | 12/2010 | Smith et al. |
| 2011/0028790 A1 | 2/2011 | Farr et al. |
| 2011/0034769 A1 | 2/2011 | Adair et al. |
| 2011/0051390 A1 | 3/2011 | Lin et al. |
| 2011/0063483 A1 | 3/2011 | Rossi et al. |
| 2011/0122301 A1 | 5/2011 | Yamura et al. |
| 2011/0149358 A1 | 6/2011 | Cheng |
| 2011/0181709 A1 | 7/2011 | Wright et al. |
| 2011/0181840 A1 | 7/2011 | Cobb |
| 2011/0184239 A1* | 7/2011 | Wright ............... A61B 1/00016 600/118 |
| 2011/0184243 A1 | 7/2011 | Wright et al. |
| 2011/0208004 A1* | 8/2011 | Feingold ............. G02B 6/0006 600/178 |
| 2011/0212649 A1 | 9/2011 | Stokoe et al. |
| 2011/0237882 A1 | 9/2011 | Saito |
| 2011/0237884 A1 | 9/2011 | Saito |
| 2011/0245605 A1 | 10/2011 | Jacobsen et al. |
| 2011/0245616 A1 | 10/2011 | Kobayashi |
| 2011/0255844 A1 | 10/2011 | Wu et al. |
| 2011/0274175 A1 | 11/2011 | Sumitomo |
| 2011/0279679 A1 | 11/2011 | Samuel et al. |
| 2011/0288374 A1 | 11/2011 | Hadani et al. |
| 2011/0291564 A1 | 12/2011 | Huang |
| 2011/0292258 A1 | 12/2011 | Adler et al. |
| 2011/0295061 A1 | 12/2011 | Haramaty et al. |
| 2012/0004508 A1 | 1/2012 | McDowall et al. |
| 2012/0014563 A1 | 1/2012 | Bendall |
| 2012/0029279 A1 | 2/2012 | Kucklick |
| 2012/0033118 A1 | 2/2012 | Lee et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0078052 A1 | 3/2012 | Cheng |
| 2012/0098933 A1 | 4/2012 | Robinson et al. |
| 2012/0104230 A1 | 5/2012 | Eismann et al. |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0155761 A1 | 6/2012 | Matsuoka |
| 2012/0157774 A1 | 6/2012 | Kaku |
| 2012/0172665 A1 | 7/2012 | Alyn et al. |
| 2012/0194686 A1 | 8/2012 | Liu et al. |
| 2012/0197080 A1 | 8/2012 | Murayama |
| 2012/0200685 A1 | 8/2012 | Kawasaki et al. |
| 2012/0209071 A1 | 8/2012 | Bayer et al. |
| 2012/0242975 A1 | 9/2012 | Min et al. |
| 2012/0262621 A1 | 10/2012 | Sato et al. |
| 2012/0281111 A1 | 11/2012 | Jo et al. |
| 2012/0296238 A1* | 11/2012 | Chernov ............. A61B 18/1442 601/2 |
| 2012/0319586 A1 | 12/2012 | Riesebosch |
| 2012/0327270 A1 | 12/2012 | Shirakawa et al. |
| 2013/0016200 A1* | 1/2013 | Ovod ....................... A61B 1/06 348/68 |
| 2013/0018256 A1 | 1/2013 | Kislev et al. |
| 2013/0035545 A1 | 2/2013 | Ono |
| 2013/0053642 A1 | 2/2013 | Mizuyoshi et al. |
| 2013/0070071 A1 | 3/2013 | Peltie et al. |
| 2013/0126708 A1 | 5/2013 | Blanquart |
| 2013/0127934 A1 | 5/2013 | Chiang |
| 2013/0135589 A1 | 5/2013 | Curtis et al. |
| 2013/0144120 A1 | 6/2013 | Yamazaki |
| 2013/0155215 A1 | 6/2013 | Shimada et al. |
| 2013/0155305 A1 | 6/2013 | Shintani |
| 2013/0158346 A1 | 6/2013 | Soper et al. |
| 2013/0184524 A1 | 7/2013 | Shimada et al. |
| 2013/0211217 A1 | 8/2013 | Yamaguchi et al. |
| 2013/0242069 A1 | 9/2013 | Kobayashi |
| 2013/0244453 A1 | 9/2013 | Sakamoto |
| 2013/0274597 A1 | 10/2013 | Byrne et al. |
| 2013/0289347 A1* | 10/2013 | Ito ..................... A61B 1/00036 600/102 |
| 2013/0292571 A1 | 11/2013 | Mukherjee et al. |
| 2013/0296651 A1* | 11/2013 | Ito ..................... A61B 1/00036 600/109 |
| 2013/0296652 A1 | 11/2013 | Farr |
| 2013/0300837 A1 | 11/2013 | DiCarlo et al. |
| 2013/0342690 A1 | 12/2013 | Williams et al. |
| 2014/0012078 A1* | 1/2014 | Coussa ............... A61B 1/00036 600/109 |
| 2014/0022365 A1 | 1/2014 | Yoshino |
| 2014/0031623 A1 | 1/2014 | Kagaya |
| 2014/0005532 A1 | 2/2014 | Choi et al. |
| 2014/0052004 A1 | 2/2014 | D'Alfonso et al. |
| 2014/0066711 A1 | 3/2014 | Farin et al. |
| 2014/0073852 A1 | 3/2014 | Banik et al. |
| 2014/0073853 A1 | 3/2014 | Swisher et al. |
| 2014/0078278 A1 | 3/2014 | Lei |
| 2014/0088363 A1 | 3/2014 | Sakai et al. |
| 2014/0094649 A1* | 4/2014 | Ito ....................... A61B 5/6885 600/103 |
| 2014/0104466 A1 | 4/2014 | Fossum |
| 2014/0110485 A1 | 4/2014 | Toa et al. |
| 2014/0142383 A1 | 5/2014 | Blumenzweig et al. |
| 2014/0160318 A1 | 6/2014 | Blanquart et al. |
| 2014/0163319 A1 | 6/2014 | Blanquart et al. |
| 2014/0198249 A1 | 7/2014 | Tanaka et al. |
| 2014/0203084 A1 | 7/2014 | Wang |
| 2014/0225215 A1 | 8/2014 | Chien et al. |
| 2014/0267655 A1 | 9/2014 | Richardson et al. |
| 2014/0267851 A1 | 9/2014 | Rhoads |
| 2014/0267890 A1 | 9/2014 | Lelescu et al. |
| 2014/0268860 A1 | 9/2014 | Talbert et al. |
| 2014/0275764 A1 | 9/2014 | Shen et al. |
| 2014/0288365 A1 | 9/2014 | Henley et al. |
| 2014/0300698 A1 | 10/2014 | Wany |
| 2014/0316197 A1 | 10/2014 | St. George et al. |
| 2014/0316199 A1 | 10/2014 | Kucklick |
| 2014/0354788 A1 | 12/2014 | Yano |
| 2014/0364689 A1 | 12/2014 | Adair et al. |
| 2015/0237245 A1 | 8/2015 | Renard et al. |
| 2015/0271370 A1 | 9/2015 | Henley et al. |
| 2016/0183775 A1 | 6/2016 | Blanquart et al. |
| 2017/0085853 A1 | 3/2017 | Blanquart et al. |
| 2017/0230574 A1 | 8/2017 | Richardson et al. |
| 2019/0028621 A1 | 1/2019 | Henley et al. |
| 2019/0133416 A1 | 5/2019 | Henley et al. |
| 2019/0174058 A1 | 6/2019 | Richardson et al. |
| 2019/0253685 A1 | 8/2019 | Blanquart et al. |

FOREIGN PATENT DOCUMENTS

| | | |
|---|---|---|
| CN | 201239130 Y | 5/2009 |
| CN | 101449575 A | 6/2009 |
| CN | 101634749 A | 1/2010 |
| CN | 101755448 A | 6/2010 |
| CN | 102469932 A | 5/2012 |
| CN | 103185960 A | 7/2013 |
| EP | 0660616 A2 | 6/1995 |
| EP | 0904725 A1 | 3/1999 |
| EP | 1079255 A2 | 2/2001 |
| EP | 1116473 A2 | 7/2001 |
| EP | 1637062 A1 | 3/2006 |
| EP | 1712177 A1 | 10/2006 |
| EP | 1819151 A1 | 8/2007 |
| EP | 2359739 A1 | 8/2011 |
| EP | 2371268 A1 | 8/2011 |
| EP | 3459431 A1 | 3/2014 |
| JP | 63-234941 | 9/1988 |
| JP | H04-039789 | 4/1992 |
| JP | H07-240931 | 9/1995 |
| JP | 1995-240931 | 3/1997 |
| JP | 2000-051150 A | 2/2000 |
| JP | 2000-199863 A | 7/2000 |
| JP | 2000270230 | 9/2000 |
| JP | 2001-308531 A | 11/2001 |
| JP | 2002-020816 A | 1/2002 |
| JP | 2002-028125 A | 1/2002 |
| JP | 2002-045329 A | 2/2002 |
| JP | 2002-112961 A | 4/2002 |
| JP | 2005-204741 A | 8/2005 |

(56) References Cited

FOREIGN PATENT DOCUMENTS

| | | |
|---|---|---|
| JP | 2007-029746 A | 2/2007 |
| JP | 2007143963 A | 6/2007 |
| JP | 2007-240931 A | 9/2007 |
| JP | 2008514304 | 5/2008 |
| JP | 2008-153313 A | 7/2008 |
| JP | 2008264539 A | 11/2008 |
| JP | 2008295929 A | 12/2008 |
| JP | 2009-537283 A | 10/2009 |
| JP | 2010-17377 A | 1/2010 |
| JP | 2010-068992 A | 4/2010 |
| JP | 2010-125284 A | 6/2010 |
| JP | 2010-158415 A | 7/2010 |
| JP | 2011-055327 A | 3/2011 |
| JP | 2011514605 | 5/2011 |
| JP | 2012-000160 A | 1/2012 |
| JP | 2012024450 | 2/2012 |
| JP | 2013-27432 A | 2/2013 |
| JP | 2011-267098 A | 6/2013 |
| JP | 2014514782 | 6/2014 |
| JP | 5682812 B2 | 1/2015 |
| JP | 2015525642 | 9/2015 |
| JP | A61-62440 | 6/2017 |
| MX | 2015001195 A | 1/2016 |
| MX | 346174 | 3/2017 |
| WO | 1996005693 | 2/1996 |
| WO | 2006037034 A2 | 4/2006 |
| WO | 2009018613 A1 | 2/2009 |
| WO | 2009115885 A2 | 9/2009 |
| WO | 2009120228 A1 | 10/2009 |
| WO | 2012043771 A1 | 4/2012 |
| WO | 2012137845 A1 | 10/2012 |

OTHER PUBLICATIONS

Blumenfeld, et al. Three-dimensional image registration of MR proximal femur images for the analysis of trabecular bone parameters. Oct. 2008. [retrieved on Jul. 30, 2014] Retrieved from the internet: <URL: http://www.ncbi.nlm.nih.gov/pmc/articles/PMC2673590/>.

* cited by examiner

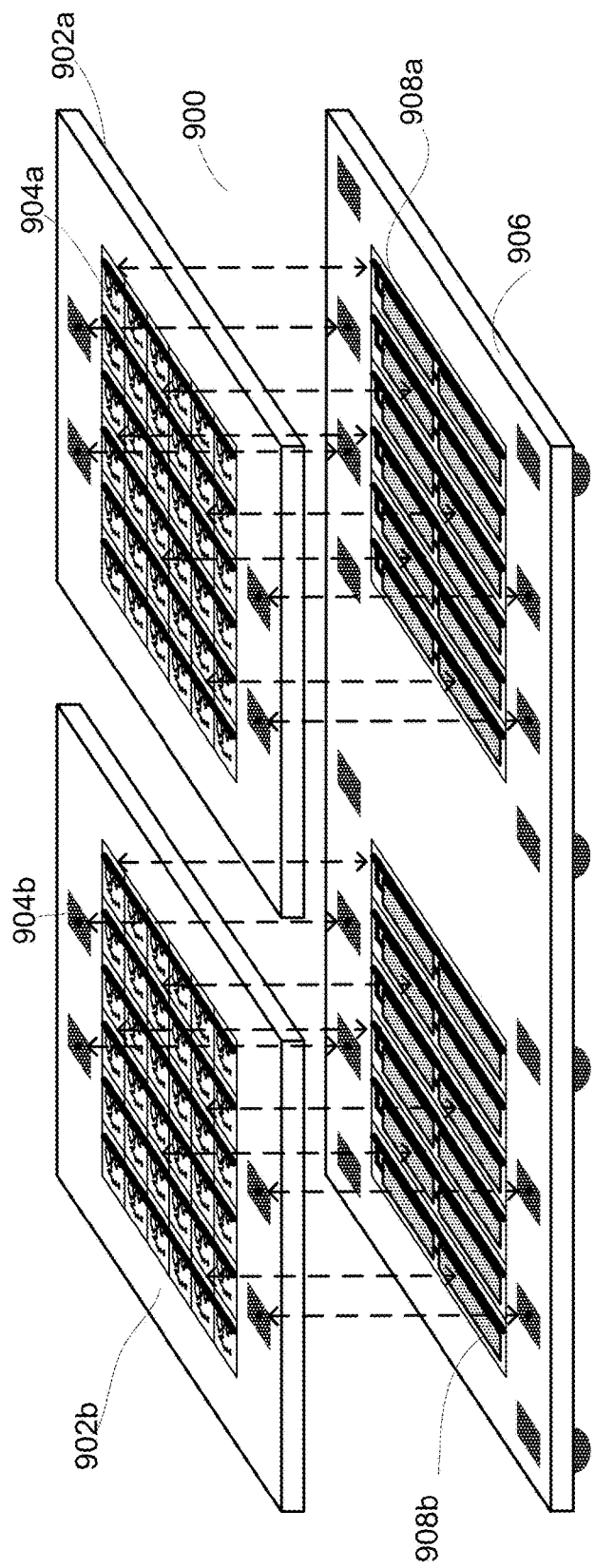
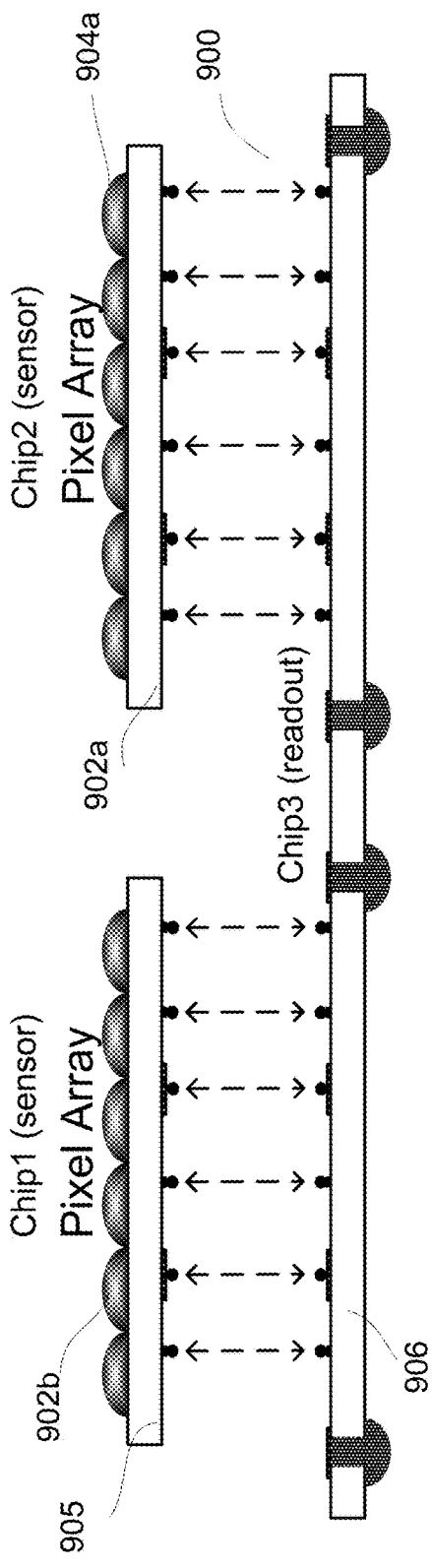
FIG. 9A
FIG. 9B

SCOPE SENSING IN A LIGHT CONTROLLED ENVIRONMENT

CROSS-REFERENCE TO RELATED APPLICATIONS

This application is a division of U.S. application Ser. No. 14/214,334, filed Mar. 14, 2014, and claims the benefit of U.S. Provisional Application No. 61/791,685, filed Mar. 15, 2013, which are hereby incorporated herein by reference in their entireties, including but not limited to those portions that specifically appear hereinafter, the incorporation by reference being made with the following exception: In the event that any portion of the above-referenced applications is inconsistent with this application, this application supersedes said above-referenced applications.

STATEMENT REGARDING FEDERALLY SPONSORED RESEARCH OR DEVELOPMENT

Not Applicable.

BACKGROUND

Current minimally invasive surgical procedures rely on endoscopes for visualization of the surgical site. In the arthroscopy, laparoscopy, urology, gynecology, and ENT (ear, nose, and throat) specialties, rigid endoscopes are primarily used. A rigid endoscope is constructed of an inner lumen containing multiple glass lens elements for visualization and an outer lumen containing a bundle of fiber optic strands for carrying light from a light source to the surgical site.

Conventional surgical light systems are very inefficient. From the light engine, which is typically a metal halide bulb, halogen bulb, xenon bulb, or LED(s) (light emitting diode), to the surgical site over ninety-five percent of the light is lost. These losses occur at multiple locations, the first being at the optic placed in front of the light engine to gather the light from a wide dispersion angle and focus it into a collimated beam with a diameter small enough to transmit to a fiber optic light cable. The second loss point is the junction of the focusing optic and the aforementioned fiber optic light cable. The fiber optic light cable is a bundle, typically with a diameter of five millimeters, of small fiber optic strands and measures one to three meters in length. The third loss point is over the length of the fiber bundle due to the attenuation rate of the bulk fiber strands. The fiber optic light cable transmits light from the light source to the endoscope in sterile field. The fourth loss point is the junction between the light cable and the proximal end of the endoscope.

Due to the losses in the light transmission path, the light source must generate a significant amount of light. This results in a significant amount of heat generated, particularly at each of the junction points and at the distal tip of the scope. The heat generated, specifically at the distal scope tip and at the junction between the light cable and scope, can present a safety risk to the surgical patient. The heat is such that if the scope is inadvertently rested on the patient for a period of time, a burn can occur. This is an issue with all conventional light sources and every year a few such incidents occur and are reported to the FDA (Food and Drug Administration).

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIGS. 9A and 9B illustrate a perspective view and a side view, respectively, of an implementation of an imaging sensor having a plurality of pixel arrays for producing a three dimensional image, wherein the plurality of pixel arrays and the image sensor are built on a plurality of substrates.

DETAILED DESCRIPTION

Figure 1:
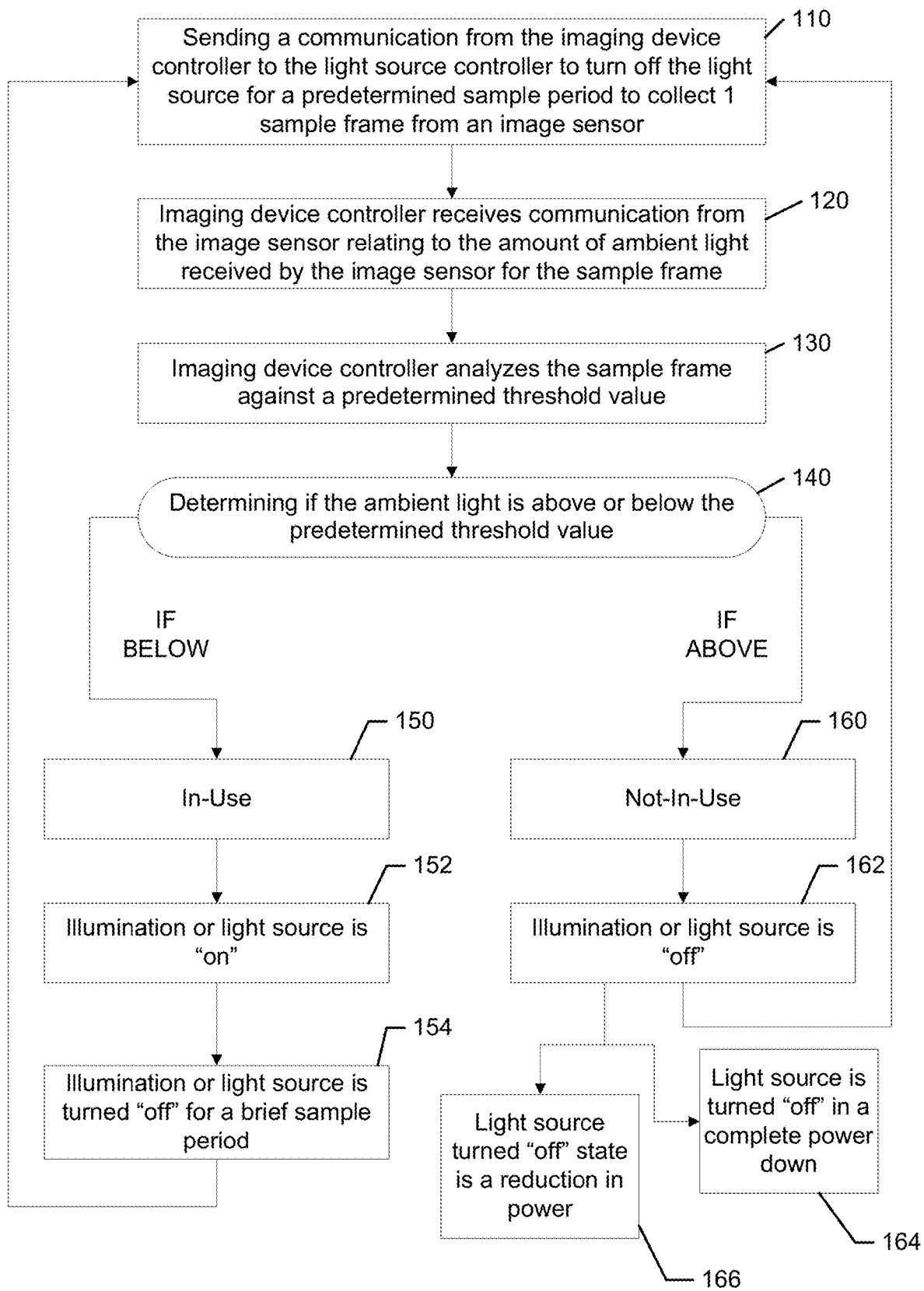
FIG. 1 illustrates a flow chart of an example method for controlling power to an endoscopic light source in a light controlled environment according to one implementation.

The disclosure extends to methods, systems, and computer program products for detecting whether an endoscopic illumination or light source is in use (inside the body of a patient) versus not in use (outside the body of a patient). The methods, systems and computer program products rely on the fact that the working environment is lit solely by the endoscope and its components. Thus, communication between the illumination or light source controller and the imaging device, such as a surgical camera, is required. In the following description of the present disclosure, reference is made to the accompanying drawings, which form a part hereof, and in which is shown by way of illustration specific implementations in which the disclosure may be practiced. It is understood that other implementations may be utilized and structural changes may be made without departing from the scope of the present disclosure.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

For safety and power consumption reasons, what is needed are methods and systems for detecting when an illumination or light source is in use and when it is not in use. As will be seen, the disclosure provides methods and systems that can do this in an efficient and elegant manner.

Referring now to the figures, it will be appreciated that the disclosure relates to a detection mechanism for operating the illumination source when an endoscope is in use (inside the body of a patient) versus not in use (outside the body of a patient). The disclosure relies on the fact that the working environment is lit solely by the endoscope and its components. Thus, communication between the illumination or light source controller and the imaging device, such as a surgical camera, is required.

For safety reasons it is preferable to have the light source off while the endoscope is not in use. This removes the risk of burning a patient if, for example, the user inadvertently leaves the endo scope resting on the patient while performing other tasks. Every year there are reported cases of patient burns resulting from such misuse of conventional endoscopic video systems.

When the light is turned off and the endoscope is outside the body, the sensor will detect ambient light. Conversely, when the light is turned off and the endoscope is inside the body, the sensor will not detect any light (or will detect only a very low level of light). Based on this logic, if the camera knows that the light is off during a specific period of time the frame(s) from that time period can be analyzed and the level of light gathered in the frame(s) will show the scope location.

Knowing the location of the scope (inside or outside the body) allows the system to keep the light source off while outside the body and only turn the light source on when the endoscope is put into the body for use.

Alternately, the light source output intensity can be reduced to a low, safe level while the scope is outside the body and then increased to a high level when inside the body and in use. This implementation may be preferred for usability reasons. Users who are not familiar with the system described herein may suspect a functional problem with the system if the light source is completely off while the scope is not in use.

Figure 4:
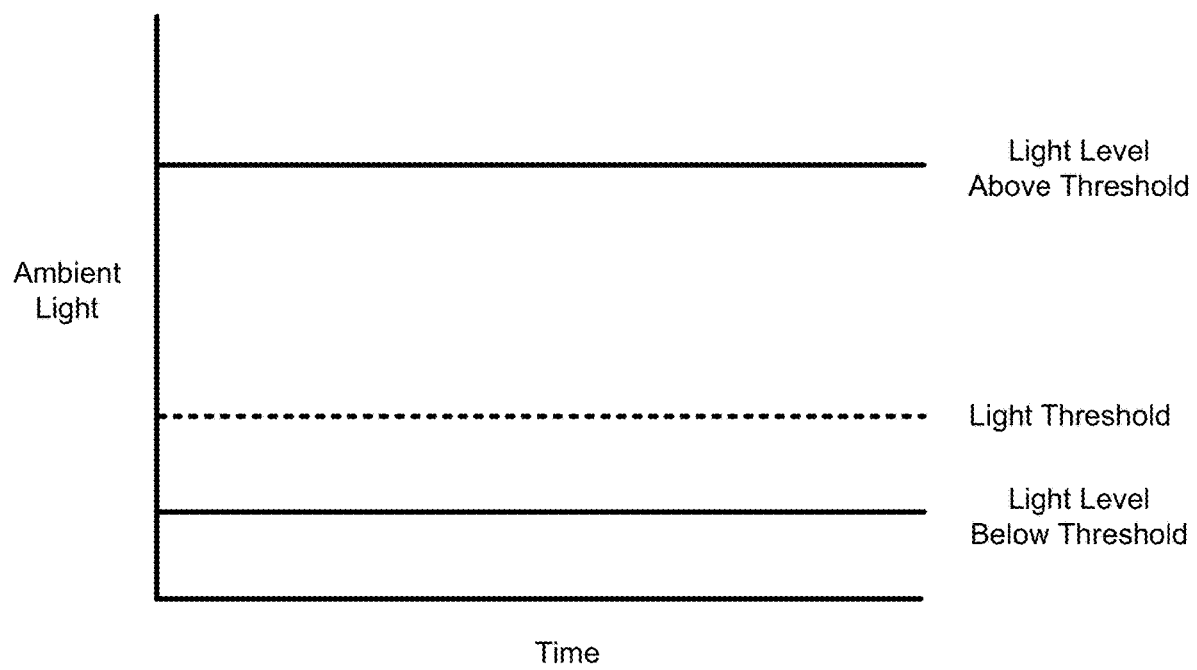
FIG. 4 illustrates a light threshold value and comparison chart of an example method according to one implementation.

Referring now to FIG. 1, there is illustrated a method for controlling power to an endoscopic light source in a light controlled environment. As illustrated in the figure, at 110 the method may comprise sending an electric communication signal from an imaging device controller to a light source controller at a specified interval. It will be appreciated that the signal may be an instruction to turn off the light source for a predetermined sample period during which a single sample frame or a plurality of sample frames may be collected from an image sensor. At 120, the imaging device controller may receive a communication or data from the image sensor. Data may be collected from the image sensor for a single frame or a plurality of frames obtained during the predetermined sample period. The data may be related to an amount of ambient light received by the image sensor. At 130, the imaging device controller may analyze the sample frame or plurality of frames against a predetermined or predefined light threshold value. Analyzing the single frame or plurality of frames obtained during the predetermined sample period against a specified, predetermined threshold value is also illustrated in FIG. 4. The operation of the light source may be controlled based on the data received from the image sensor.

At 140, a determination is made by the image device controller. If the ambient light is above or below the predetermined light threshold value, then one of two processes may be followed. Specifically, if the measured light from the image sensor is determined to be below the predetermined light threshold value, then at 150 it is determined that the image sensor is in a light deficient environment. When it is determined that the light source is in a light deficient environment, that determination signifies that the imaging device is in-use. At 152, the light source remains in an operable state, thereby providing light to the light deficient environment. At 154, the light source may be turned off for a predetermined sample period and the process starts over again.

At 140, if the measured light from the image sensor is determined to be above the predetermined light threshold value, then at 160 it is determined that the image sensor is not in-use because it is outside of a light deficient environment. In such a circumstance, at 162, the light source is turned off, thereby providing a safety mechanism for controlling power to the light source. It will be appreciated that in one implementation, at 164, the turned off state may be a complete power down of the light source. In another implementation, at 166, the turned off state may be a reduction in power to the light source, such that the light source is only emitting a small amount of light energy. As noted previously, the method may include sampling at a plurality intervals, such as a second interval, to determine whether data received from the image sensor regarding a single frame is above or below the predetermined light threshold value.

Figure 2:
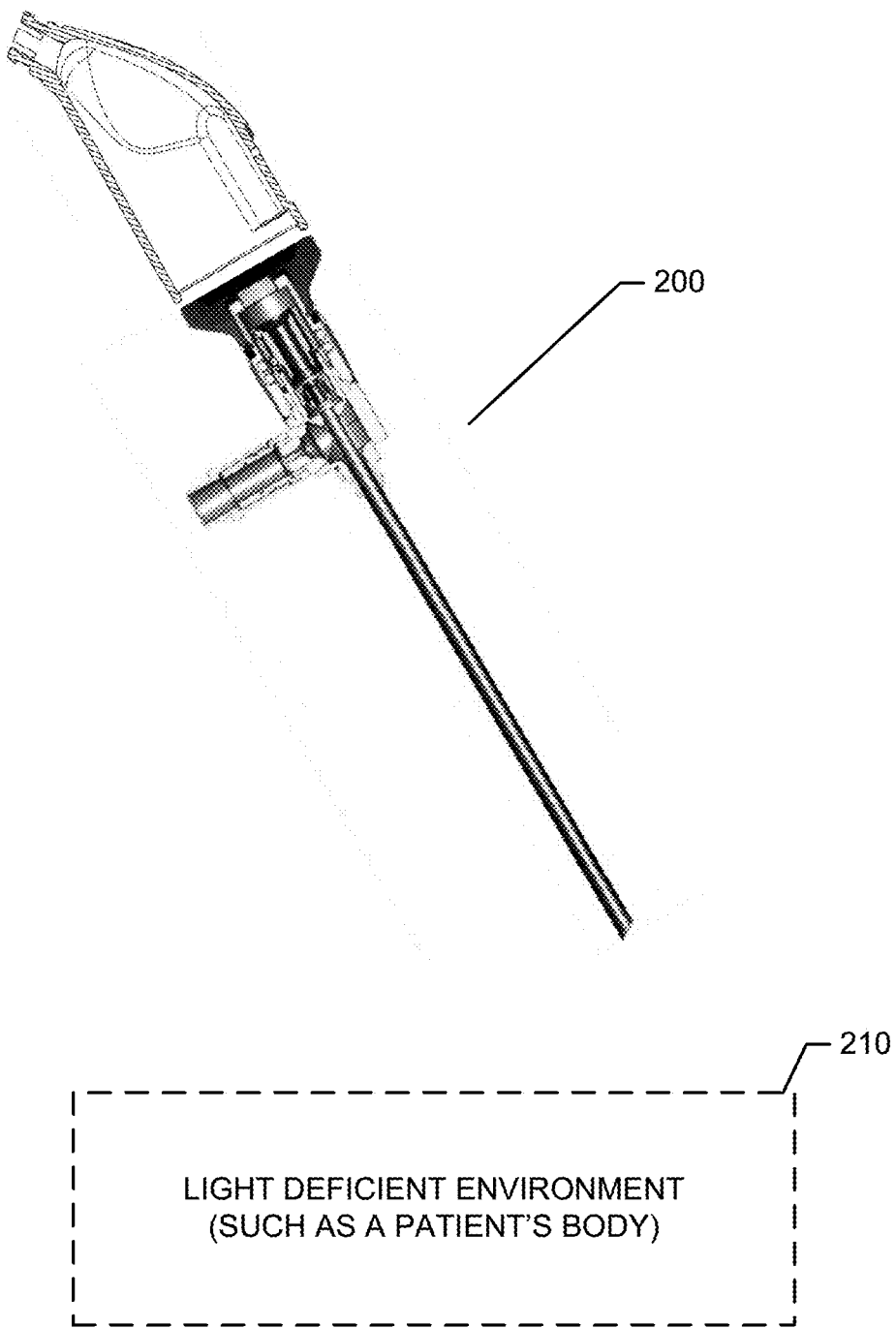
FIG. 2 illustrates an imaging device located outside of a light deficient environment, such as a patient's body, wherein the light source is turned off due to the amount of ambient light present in accordance with the system and method described herein.
Figure 3:
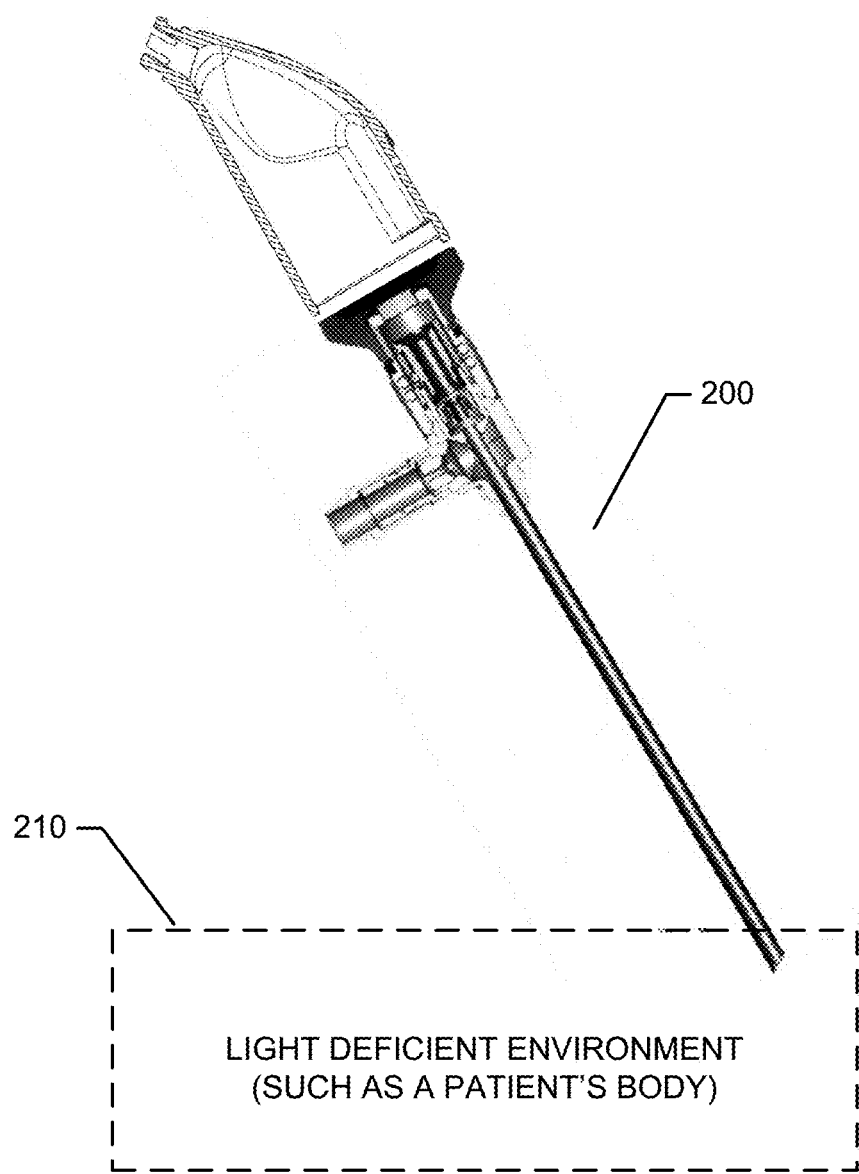
FIG. 3 illustrates an imaging device located in a light deficient environment, such as a patient's body, wherein the light source is turned on due to the lack of ambient light present in accordance with the system and method described herein.

Referring now to FIGS. 2 and 3, it will be appreciated that in one implementation, the default mode when the endoscopic light source system starts-up is for the light source to be turned off or in an off state. At this time, the imaging device controller is in communication with the light source controller and knows the light source is turned off or in an off state. At specified intervals, such as for example every $30^{th}$ frame, the imaging device captures a single frame and analyzes the light level against the predetermined light threshold value. It is to be understood that the specified intervals may be at any frequency that produces the desired functional result. Further, it is to be understood that the light threshold value may be defined as an amount of total light received by the image sensor; or the threshold value may be defined as an average of an amount of light received per pixel on the image sensor.

If the light source is determined to be not in-use as illustrated in FIG. 2, then the imaging device controller communicates information, instructions or data to the light source controller to remain off or in an off state. Conversely, if the light source is determined to be in-use as illustrated in FIG. 3, then the imaging device controller communicates information, instructions or data to the light source controller to turn on. Once the light source is turned on, a new pattern begins. Thus, at predetermined, specified intervals the light source is turned off for a predetermined sample period during which time the imaging device captures a single frame and analyzes the light level against the predetermined threshold value. It is understood that the sample period may be any length that is long enough for the imaging device to capture one frame, but short enough that is does not negatively affect video quality or user experience. As illustrated best in FIG. 4, if the data received from the image sensor is below the predetermined threshold value, then the imaging device recognizes the light source as being in-use in a light deficient environment, and the imaging device controller communicates with the light source controller to turn on. Whereas, if the data received from the image sensor is above the predetermined threshold value, then the image device recognizes the light source as being not-in-use and is outside the light deficient environment, and the imaging device controller communicates with the light source controller to remain off.

Figure 5:
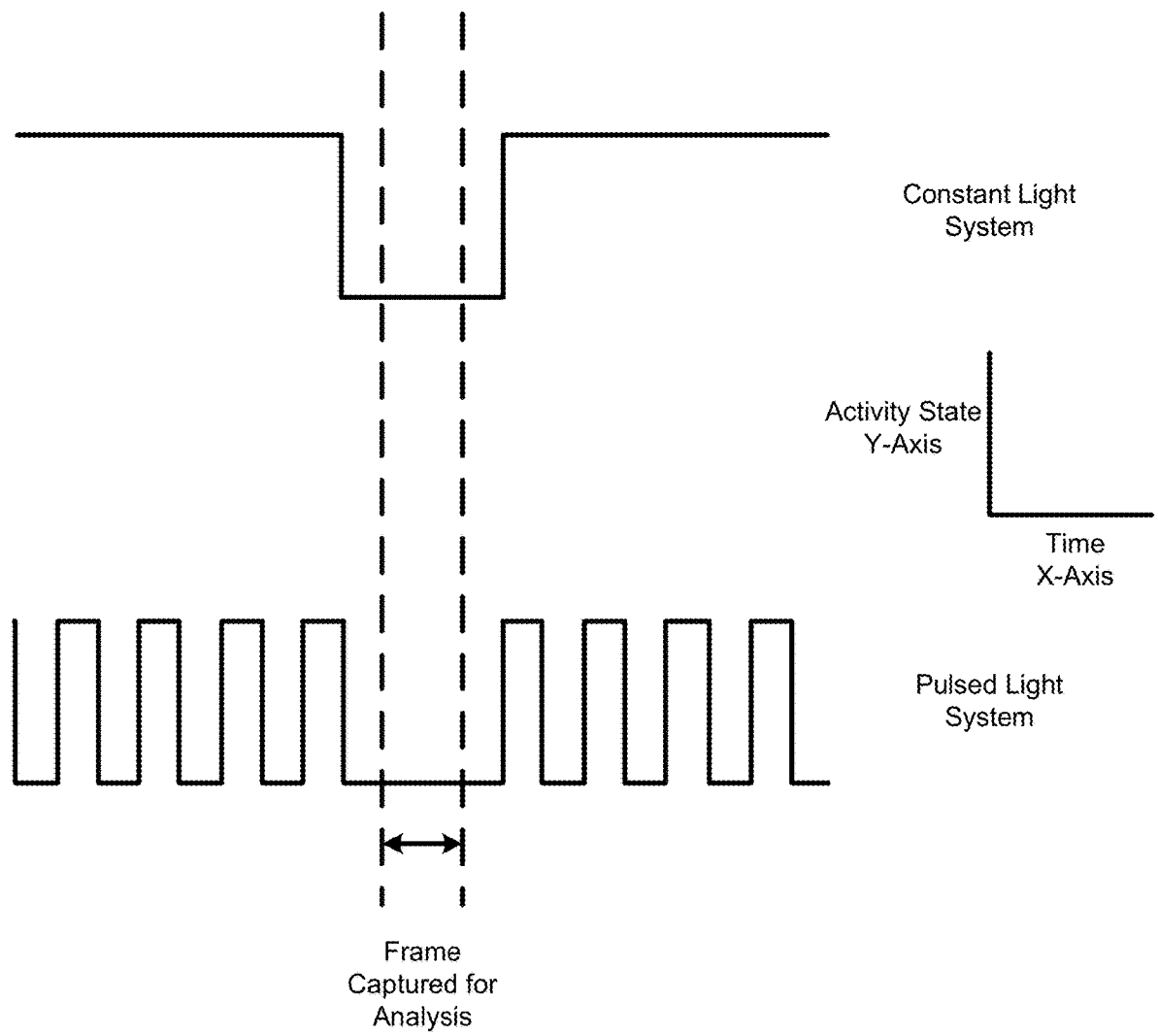
FIG. 5 illustrates an interval in a constant light system and a pulsed light system wherein a frame is captured for analysis in accordance with the system and method described herein.

Referring now to FIG. 5, the light source may be a pulsed light system. In an implementation, the light in the pulsed light system may be obtained from laser light. In an implementation, the light in the pulsed light system may be obtained from one or more light emitting diodes. In another implementation, the light source may be a constant light system.

It will be appreciated that the sampling interval may be every $30^{th}$ frame as described above, or it may be any other frequency that provides the desired results. It is within the scope of the disclosure for the interval frequency may be different during the "in-use" condition and the "not-in-use" condition.

In an implementation, the imaging device, such as a camera, may provide constant control over the light source. In an implementation, the light source may have a default state that is changed by the imaging device as required.

The method and system of the disclosure may require communication between the light source controller and the imaging device controller. The disclosure also contemplates use of a light source with a response time that is fast enough that the "off" pulse during the sample period, during the "in-use" condition, does not adversely affect the video quality. LED and laser light sources may be used, while a metal halide bulb, halogen bulb, or xenon bulb may not be used in this implementation.

During use, the light source can be kept on constantly with a periodic "off" pulse or the light source can be pulsed "on" during normal use, illustrated best in FIG. 5, with an "on" pulse skipped for the black frame analysis.

In an implementation, the light intensity level can be reduced to a predetermined safe level while in the "not-in-use" state. In this implementation the default mode on startup could be a low light intensity level that poses no risk of burning. Then, as previously described, at predetermined intervals the light is turned off for the sample period and this sample frame is analyzed. If the result is "not-in-use", the light is turned back on at the previous safe level and the pattern repeats. If the result is "in-use", the light is turned on at the higher functional level.

In an implementation, the light could be pulsed light of a particular colors (including, but not limited to, RBG or YCbCr) rather than white light. In this implementation it may be desirable to change from pulsed colored light while "in-use" to pulsed or constant white light while "not-in-use" using the same techniques previously described. The default mode on startup could be a low level of pulsed or constant white light. Then, as previously described, at predetermined intervals the light is turned off for the sample period and this sample frame is analyzed. If the result is "not-in-use", the white light is turned back on at the previous safe level and the pattern repeats. If the result is "in-use", the pulsed color pattern is initiated.

In an implementation, the system may be comprised of a light source that is kept in a constant on-state with a mechanical shutter providing the periodic black frame. This shutter may be controlled by the imaging device, such that there would be no imaging device control of the light source needed. This shutter could be placed at any interface in the light path from the source to the distal tip of the endoscope. In this implementation there is no restriction on light source technology because there is no requirement for the light source to have a fast response time. Instead, the mechanical shutter requires a response time that is fast enough that the "off" pulse during the sample period, during the "in-use" condition, does not adversely affect the video quality.

In any implementation, a visual or audible signal could be given to inform the user of whether the system is in the "in-use" or "not-in-use" state. Alternately, the signal could inform the user when the state changes from "in-use" to "not-in-use" or from "not-in-use" to "in-use" or both.

A black frame would disrupt the video output. During image processing, the black frame can be removed and the previous frame can be displayed in its place. Conversely, multiple frames before and/or after the black frame can be used to construct a substitute frame.

Figure 6:
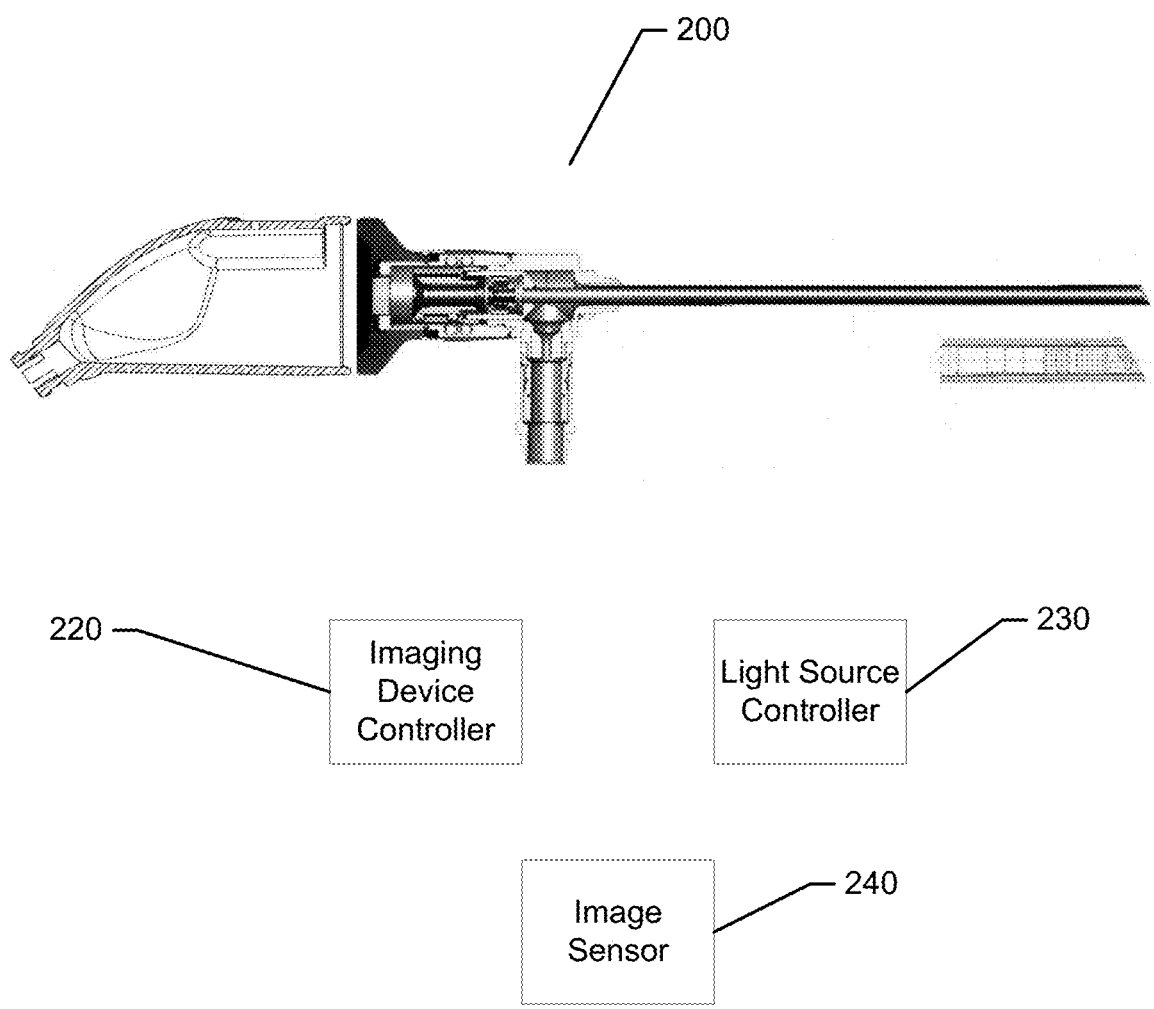
FIG. 6 illustrates a system for controlling power to an endoscopic light source in a light controlled environment according to one implementation.

Referring now to FIG. 6, a system for controlling power to an endoscopic light source in a light controlled environment is illustrated. The system may comprise an imaging device 200 comprising an imaging device controller 220, a light source comprising a light source controller 230; and an image sensor 240. It will be appreciated that the imaging device controller may cause the system to perform the following processes: send an electric communication signal to a light source controller at a specified interval; turn off the light source for a predetermined sample period based on the electric communication signal; collect data from the image sensor for a single frame obtained during the predetermined sample period, wherein the data relates to an amount of ambient light received by the image sensor; analyze the single frame obtained during the predetermined sample period against a specified, predetermined threshold value; and control the operation of the light source based on the data received from the image sensor.

Figure 7A:
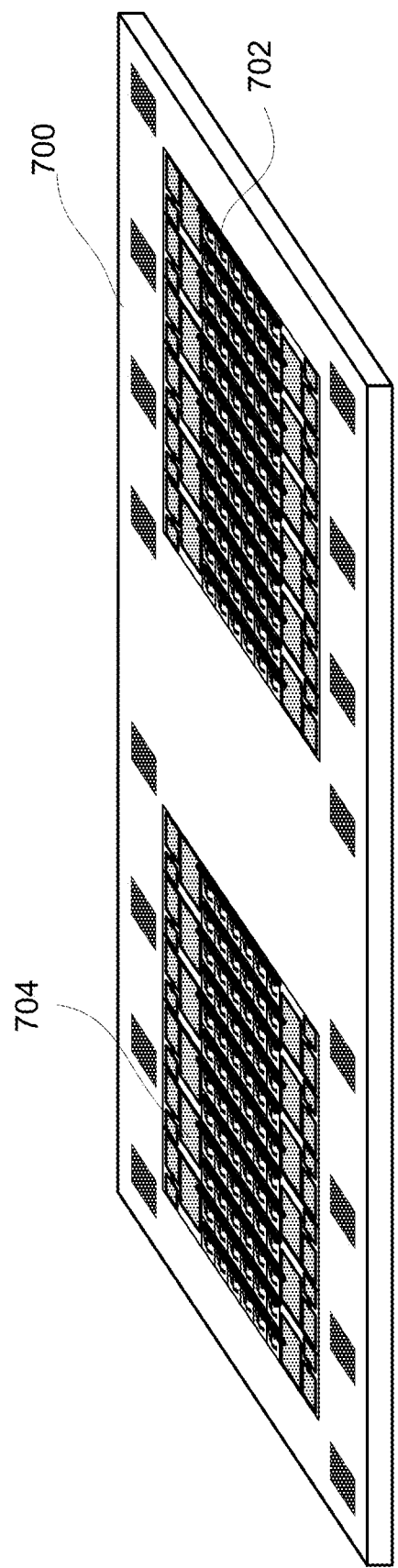
FIGS. 7A and 7B illustrate a perspective view and a side view, respectively, of an implementation of a monolithic sensor having a plurality of pixel arrays for producing a three dimensional image in accordance with the teachings and principles of the disclosure.
Figure 7B:
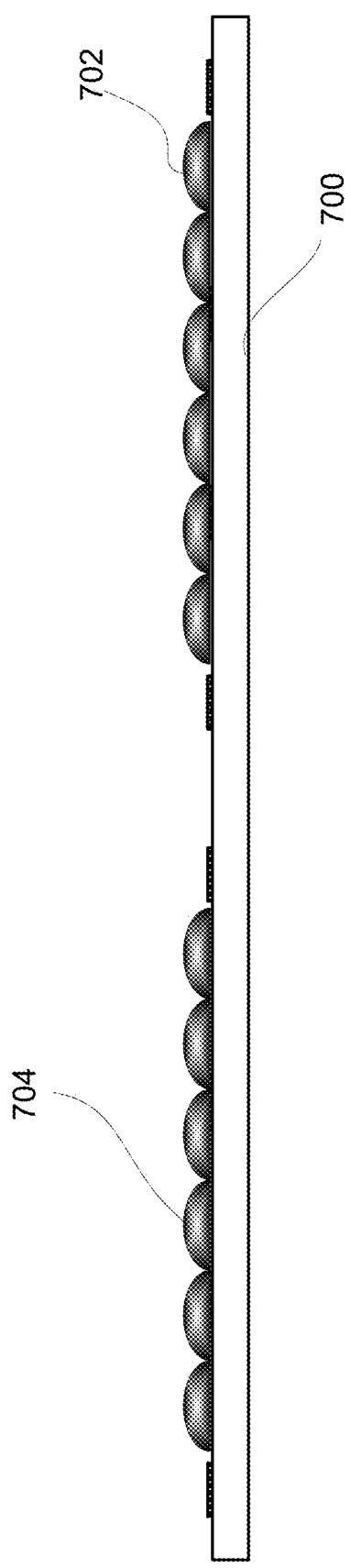

Referring now to FIGS. 7A and 7B, the figures illustrate a perspective view and a side view, respectively, of an implementation of a monolithic sensor 700 having a plurality of pixel arrays for producing a three dimensional image in accordance with the teachings and principles of the disclosure. Such an implementation may be desirable for three dimensional image capture, wherein the two pixel arrays 702 and 704 may be offset during use. In another implementation, a first pixel array 702 and a second pixel array 704 may be dedicated to receiving a predetermined range of wave lengths of electromagnetic radiation, wherein the first pixel array 702 is dedicated to a different range of wave length electromagnetic radiation than the second pixel array 704.

Figure 8A:
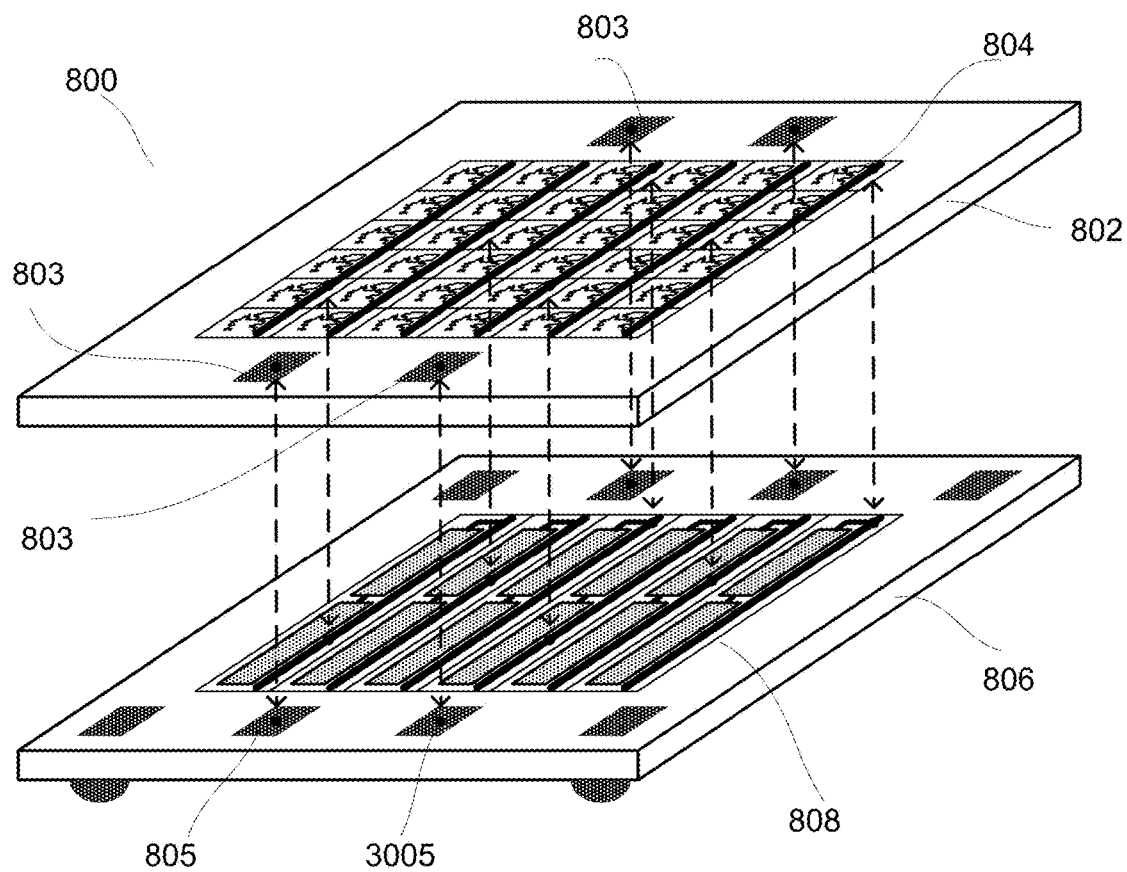
FIGS. 8A and 8B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 8B:
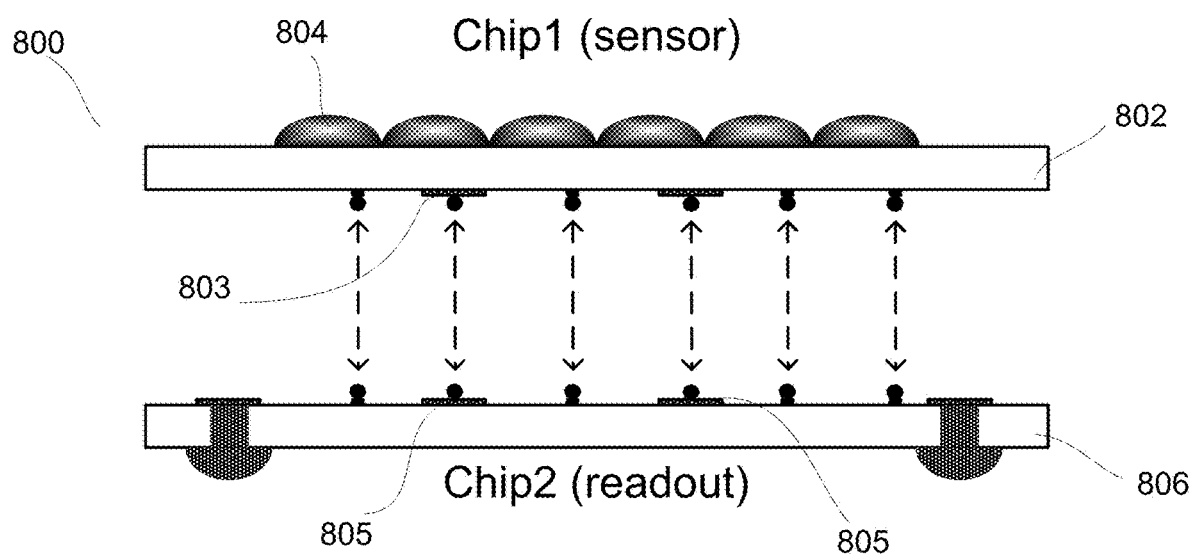

FIGS. 8A and 8B illustrate a perspective view and a side view, respectively, of an implementation of an imaging sensor 800 built on a plurality of substrates. As illustrated, a plurality of pixel columns 804 forming the pixel array are located on the first substrate 802 and a plurality of circuit columns 808 are located on a second substrate 806. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 802 of the two substrates/chips may be processed using an image CMOS process. The first substrate/chip 802 may be comprised either of a pixel array exclusively or a pixel array surrounded by limited circuitry. The second or subsequent substrate/chip 806 may be processed using any process, and does not have to be from an image CMOS process. The second substrate/chip 806 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 802 may be stacked with the second or subsequent substrate/chip 806 using any three-dimensional technique. The second substrate/chip 806 may support most, or a majority, of the circuitry that would have otherwise been implemented in the first image CMOS chip 802 (if implemented on a monolithic substrate/chip) as peripheral circuits and therefore have increased the overall system area while keeping the pixel array size constant and optimized to the fullest extent possible. The electrical connection between the two substrates/chips may be done through interconnects 803 and 805, which may be wirebonds, bump and/or TSV (Through Silicon Via).

FIGS. 9A and 9B illustrate a perspective view and a side view, respectively, of an implementation of an imaging sensor 900 having a plurality of pixel arrays for producing a three dimensional image. The three dimensional image sensor may be built on a plurality of substrates and may comprise the plurality of pixel arrays and other associated circuitry, wherein a plurality of pixel columns 904a forming the first pixel array and a plurality of pixel columns 904b forming a second pixel array are located on respective substrates 902a and 902b, respectively, and a plurality of circuit columns 908a and 908b are located on a separate substrate 906. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system for controlling power to an endoscopic light source in a light controlled environment comprising:
   an imaging device comprising an imaging device controller;
   a light source comprising a light source controller;
   an image sensor;
   wherein the imaging device controller causes the system to perform the following processes:
   send an electric communication signal to a light source controller at a specified interval;
   turn off the light source for a predetermined sample period based on the electric communication signal, the predetermined sample period having a length sufficient for the image sensor to capture at least a single frame;
   collect data from the image sensor for the single frame obtained during the predetermined sample period, wherein the data relates to an amount of ambient light received by the image sensor;
   analyze the single frame obtained during the predetermined sample period against a specified, predetermined threshold value; and
   control the operation of the light source based on the data received from the image sensor.

2. The system of claim 1, wherein if the data received from the image sensor is below the predetermined threshold value, then the light source is recognized as being in-use by the imaging device controller and is in a light deficient environment.

3. The system of claim 2, wherein the light source remains in an operable state to thereby provide light to the light deficient environment when the data received from the image sensor is below the predetermined threshold value.

4. The system of claim 1, wherein if the data received from the image sensor is above the predetermined threshold value, then the light source is recognized as being not in-use by the imaging device controller and is outside of a light deficient environment.

5. The system of claim 4, wherein the light source is turned off, thereby providing a safety mechanism for controlling power to the light source.

6. The system of claim 1, wherein a default mode when the endoscopic light source system starts up is for the light source to be turned on.

7. The system of claim 6, wherein at predetermined, specified intervals the imaging device controller communicates with the light source controller to turn off the light source for a predetermined sample period, the imaging device captures a single frame and analyzes the light level against the predetermined threshold value.

8. The system of claim 7, wherein if the data received from the image sensor is below the predetermined threshold value, then the imaging device recognizes the light source as being in-use in a light deficient environment, and the imaging device controller communicates with the light source controller to return to the default mode.

9. The system of claim 7, wherein if the data received from the image sensor is above the predetermined threshold value, then the imaging device recognizes the light source as being not-in-use and is outside the light deficient environment, and the imaging device controller communicates with the light source controller to remain off.

10. The system of claim 1, wherein a default mode when the endoscopic light source system starts up is for the light source to be turned off.

11. The system of claim 10, wherein the imaging device controller is in communication with the light source controller.

12. The system of claim 11, wherein at specified intervals the imaging device captures the single frame and analyzes the light level against the predetermined threshold value.

13. The system of claim 12, wherein the predetermined threshold value is an amount of total light received by the image sensor.

14. The system of claim 12, wherein the predetermined threshold value is an average of an amount of light received per pixel.

15. The system of claim 10, wherein if the light source is determined to be not in-use then the imaging device controller communicates to the light source controller to remain off.

16. The system of claim 10, wherein if the light source is determined to be in-use then the imaging device controller communicates to the light source controller to turn on.

17. The system of claim 16, wherein once the light source is turned on, a light pulsing pattern begins, such that at predetermined, specified intervals the light source is turned off for a predetermined sample period, the imaging device captures a single frame and analyzes the light level against the predetermined threshold value.

18. The system of claim 17, wherein if the data received from the image sensor is below the predetermined threshold value, then the imaging device recognizes the light source as being in-use in a light deficient environment, and the imaging device controller communicates with the light source controller to turn on.

19. The system of claim 17, wherein if the data received from the image sensor is above the predetermined threshold value, then the imaging device recognizes the light source as being not-in-use and is outside the light deficient environment, and the imaging device controller communicates with the light source controller to remain off.

20. The system of claim 1, wherein the imaging device controller communicating with the system provides a user with information regarding the current state of the system.

21. The system of claim 20, wherein the information is provided visually.

22. The system of claim 20, wherein the information is provided audibly.

23. The system of claim 1, wherein the imaging device controller communicating with the system provides a user with information regarding a change in the state of the system.

24. The system of claim 23, wherein the information is provided visually.

25. The system of claim 23, wherein the information is provided audibly.

* * * * *